United States Patent
Öhrström et al.

(10) Patent No.: US 7,429,566 B2
(45) Date of Patent: Sep. 30, 2008

(54) METHOD FOR TREATING HEMOPHILIA B

(75) Inventors: Jan Öhrström, Mercer Island, WA (US); Lynn Massman Rose, Seattle, WA (US); Paul D. Bishop, Fall City, WA (US)

(73) Assignee: Zymogenetics Inc., Seattle, WA (US)

( * ) Notice: Subject to any disclaimer, the term of this patent is extended or adjusted under 35 U.S.C. 154(b) by 0 days.

(21) Appl. No.: 11/521,902

(22) Filed: Sep. 15, 2006

(65) Prior Publication Data

US 2007/0015709 A1 Jan. 18, 2007

Related U.S. Application Data

(63) Continuation of application No. 10/416,055, filed as application No. PCT/US01/47144 on Nov. 8, 2001, now abandoned.

(60) Provisional application No. 60/247,362, filed on Nov. 10, 2000.

(51) Int. Cl.
*A61K 38/37* (2006.01)

(52) U.S. Cl. .................................................. 514/12

(58) Field of Classification Search .................. None
See application file for complete search history.

(56) References Cited

U.S. PATENT DOCUMENTS 6,084,074 A * 7/2000 Kato et al. .................. 530/381

OTHER PUBLICATIONS

Beers et al., Merck Man. of Diag. and Ther., 17th ed., chapter 131, 1999.*
Karges et al., Sem. Throm. and Hemo., vol. 22(5), pp. 427-436, 1996.*
Dahlback, The Lancet, vol. 355, pp. 1627-1632 (May 6, 2000).
Beers et al., Marck Man of Diag and Ther, 17th Ed, Chapter 131 (1999).
Karges et al., Sem. Throm and Hemo, vol. 22 (5), pp. 427-436 (1996).
Encyclopedia of Molecular Biology (1994, Blackwell Science Ltd. (Cambridge MA), p. 119).
Hemostasis and Thrombosis: Basic Principles and Clinical Practice 5th Ed., 2006, Lippincott, Williams & Wilkins, p. 131 and 143-150.
Fibrogammin® P package insert.
Hemostasis and Thrombosis: Basic Principles and Clinical Practice 5th Ed., 2006, Lippincott, Williams & Wilkins, p. 325-334.
Vanscheidt, Wolfgang et al., Factor XIII-deficiency in the Blood of Venous Leg Ulcer Patients, Acta Derm Venereel, vol. 71 (Stockholm).
Lorenz, Reinhard, et al., Factor XIII in Chronic Inflammatory Bowel Diseases, Seminars in Thrombosis and Hemostasis, vol. 22 (5), pp. 451-455 (1996), Theime Medical Publishers, Inc., New York.

* cited by examiner

*Primary Examiner*—Cecilia Tsang
*Assistant Examiner*—Roy Teller
(74) *Attorney, Agent, or Firm*—Len S. Smith

(57) ABSTRACT

Use of factor XIII for treating hemophilia B. A patient having hemophilia B is treated by administering factor XIII, generally in conjunction with factor IX.

2 Claims, No Drawings

METHOD FOR TREATING HEMOPHILIA B

CROSS-REFERENCE TO RELATED PATENT APPLICATIONS

This patent application is a continuation of copending and commonly owned U.S. patent application Ser. No. 10/416,055, filed May 7, 2003, which is the US national phase of International Patent Application PCT/US01/47144, filed Nov. 8, 2001, and claims the benefit of U.S. Provisional Patent Application 60/247,362, filed Nov. 10, 2000, each of which being hereby incorporated by reference.

BACKGROUND OF THE INVENTION

Hemophilia B is an inherited disorder of blood coagulation characterized by a permanent tendency to hemorrhage due to a defect in the blood coagulation mechanism. Hemophilia B is caused by a deficiency in factor IX. Factor IX is a single-chain, 55,000 Da proenzyme that is converted to an active protease (factor IXa) by factor XIa or by the tissue factor VIIa complex. Factor IXa then activates factor X in conjunction with activated factor VIII. Hemophilia B occurs in 1 in 30,000 male births. Since the disease displays X-linked recessive inheritance, females are very rarely affected.

Hemophilic bleeding occurs hours or days after injury, can involve any organ, and, if untreated may continue for days or weeks. This can result in large collections of partially clotted blood putting pressure on adjacent normal tissues and can cause necrosis of muscle, venous congestion, or ischemic damage to nerves.

Hemophilia B is treated by administering to the patient either recombinant or plasma-derived factor IX.

However, there are times when treating such patients with factor IX produces less than satisfactory results, and hemorrhaging continues. Thus, there is a need to develop additional therapies for treating hemophilia B.

DESCRIPTION OF THE INVENTION

The present invention fills this need by administering to patients with hemophilia B factor XIII in conjunction with factor IX, and by administering to patients afflicted with hemophilia B factor XIII in conjunction with factor IX.

The teachings of all of the references cited herein are incorporated in their entirety by reference.

Hemophilia B is heterogeneous in both its clinical severity and molecular pathogenesis. Clinical severity roughly correlates with the level of factor IX activity. In severe hemophilia B, the patient will have less than 1% normal factor IX in his plasma (about 0.1 U/ml of plasma). Once a bleeding disorder has been determined to be present, the physician must determine what is the cause of the disorder. For diagnostic purposes, the hemostatic system is divided into two parts: the plasma coagulation factors, and platelets. With the exception of factor XIII deficiency, each of the known defects in coagulation proteins prolongs either the prothrombin time (PT), or partial thromboplastin time (PTT), or both of these laboratory-screening assays. A PT is performed by addition of a crude preparation of tissue factor (commonly an extract of brain) to citrate-anticoagulated plasma, recalcification of the plasma, and measurement of the clotting time. A PTT assay is performed by the addition of a surface-activating agent, such as kaolin, silica, or ellagic acid, and phospholipid to citrate-anticoagulated plasma. After incubation for a period sufficient to provide for the optimal activation of the contact factors, the plasma is recalcified and the clotting time measured. The name of the PTT assay emanates from the phospholipid reagents being originally derived from a lipid-enriched extract of complete thromboplastin, hence the term partial thromboplastin. The PTT assay is dependent on factors of both the intrinsic and common pathways. The PTT may be prolonged due to a deficiency of one or more of these factors or to the presence of inhibitors that affect their function. Although its commonly stated that decreases in factor levels to approximately 30% of normal are required to prolong the PTT, in practice the variability is considerable in sensitivity of different commercially available PTT reagents to the various factors. In fact, the levels may vary from 25% to 40%. See, Miale J B: Laboratoiy Medicine-Hematology. 6.sup.th Ed., (CV Mosby, St. Louis, Mo., 1982). If the PT and PTT are abnormal, quantitative assays of specific coagulation proteins are then carried out using the PT or PTT tests and plasma from congenitally deficient individuals as substrate. The corrective effect of varying concentration of patient plasma is measured and expressed as a percentage of normal pooled plasma standard. The interval range for most coagulation factors is from 50 to 150 percent of this average value, and the minimal level of most individual factors needed for adequate hemostasis is 25 percent.

Dosage in Factor IX Replacement Therapy

One unit of factor IX is defined as the amount of factor IX activity present in 1 ml of pooled normal human plasma and is equivalent to 100% activity. The dose of factor IX needed to achieve a desired level of activity can be calculated based on estimation of the patient's plasma volume and knowledge of factor IX kinetics.

Plasma volume may be estimated as 5% of body weight or 50 ml/kg body weight. Thus the plasma volume of a 70 kg patient is approximately 3,500 ml. By definition, for such a patient to have 100% factor IX activity, 1 U/ml of plasma or a total of 3,500 U of factor IX must be present in this plasma volume. If severe hemophilia B is present, it may be assumed that the initial factor IX activity is zero. Thus, to obtain 100% activity, at least 3,500 U of factor IX must be administered. Because of rapid redistribution into the extravascular space and adsorption onto endothelial cells of vessel walls, however, only about 50% of the infused factor IX remains in circulation after a short period. Therefore, to obtain 100% activity, the initial dose should be about 7,000 U of factor IX. To generalize to any size patient with any initial factor IX level and any desired target level, infusion of 1 U/kg of body weight of factor IX will raise the factor IX level approximately 1%. For example, a dose of 1,750 U would raise a 50-kg patient from a starting factor IX level of 15% to a target of 50% activity.

After its initial rapid redistribution, factor IX has a second phase half-life of approximately 18-24 hours. Because the variability in this measurement is significant, it is best determined in each individual patient to allow proper dosing. Based on these data, the factor IX level of a patient raised to 100% activity would be expected to decay to 50% by approximately 24 hours after infusion of the initial dose. A second bolus one-half the amount of the first should then raise the level from 50% to 100%. Factor IX is commonly administered in boluses every 12-24 hours. For the recombinant factor IX, BENEFFIX™, Genetics Institute, Cambridge, Mass., the number of factor IX International Units (IU) to be administered should be the percentage of factor IX increase desired multiplied by 1.2 IU/kg of body weight.

Factor IX is produced by a number of companies in both a recombinant and plasma-derived formulations. Among these are the following: BENEFIX.RTM. (recombinant product produced by Genetics Institute, Cambridge, Mass.), MONOINE™ Concentrate (Centeon, King of Prussia, Pa.), ALPHANINE™ SD (Alpha Therapeutic Corp. Los Angeles, Calif.), BEBULNE VH IMMUNO™ (Immuno, Rochester, Minn.), KONYNE 80™ (Bayer Corporation, Biological, West Haven, Conn.), PROPLEX T™ (Baxter Healthcare, Glendale, Calif.) and PROFILNINE SD™ (Alpha Corporation).

Treatment of Hemophilia B with Factor IX and Factor XIII

The method of the present invention improves upon the above-described treatment of hemophilia B by administering factor XIII in conjunction with factor IX. The factor XIII can be administered at any time alone or at the same time as factor IX either to stop a hemorrhage or for prophylaxis.

Factor XIII, also known as fibrin-stabilizing factor, circulates in the plasma at a concentration of 10-20 mg/ml. The protein exists in plasma as a tetramer comprised of two A subunits and two B subunits. Each subunit has a molecular weight of 85,000 Da, and the complete protein has a molecular weight of approximately 330,000 Da. Factor XIII catalyzes the cross-linkage between the γ-glutamyl and ϵ-lysyl groups of different fibrin strands. The catalytic activity of factor XIII resides in the A subunits. The B subunits act as carriers for the A subunits in plasma factor XIII. Recombinant factor XIII can be produced according to the process described in European Patent No. 0 268 772 B1. See also U.S. Pat. No. 6,084,074. The level of factor XIII in the plasma can also be increased by administering a factor XIII concentrate derived from human placenta called FIBROGAMMIN™ (Aventis Corp.) or by administration of recombinant factor XIII.

A pharmaceutical composition comprising factor XIII can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. A suitable pharmaceutical composition of factor XIII will contain 1 mM EDTA, 10 mM Glycine, 2% sucrose in water. An alternative formulation will be a factor XIII composition containing 20 mM histidine, 3% wt/volume sucrose, 2 mM glycine and 0.01% wt/vol. polysorbate, pH 8. The concentration of factor XIII should preferably be 1-10 mg/mL, more preferably about 5 mg/mL.

Other suitable carriers are well known to those in the art. See, for example, Gennaro (ed.), Remington's Pharmaceutical Sciences, 19th Edition (Mack Publishing Company 1995).

Administration of Factor XIII

Factor XIII can be administered intravenously, intramuscularly or subcutaneously to treat hemophilia B. When administering therapeutic proteins by injection, the administration may be by continuous infusion or by single or multiple boluses. The levels of factor XIII in an individual can be determined by assays well known in the art such as the BERICHROM™0 F XIII assay (Dade Behring Marburgh GmbH, Marburg, Germany). The normal adult has an average of about 45 ml of plasma per kg of body weight. Each liter of blood has 1000 units (U) of factor XIII. The amount of factor XIII administered should be enough to bring an individual's level of factor XIII in the plasma to 100% of normal plasma or slightly above to 1-5% above normal, A dose of 0.45 U/kg would raise the level of factor XIII by about 1% compared to normal. One unit of factor XIII is about 10 μg of recombinant factor XIII, which contains only the dimerized A subunit. Thus, to raise the level of factor XIII by 1%, one would administer about 4.5 μg of the A2 subunit per kilogram weight of the individual. So to raise the level 30% of normal, one would administer 13.5 U/kg. For a 75 kg individual this would be about 1,012.5 U. Some patients may have consumptive coagulopathies that involve factor XIII losses. In such cases, a higher dosing (e.g., 1-2 U/kg-%) or multiple dosing of factor XIII (e.g., 1-2 U/kg-%-day) may be required.

What is claimed is:

1. A method for treating hemophilia B in an individual in need thereof consisting essentially of administering to the individual an effective amount of a composition comprising recombinant factor XIII as the sole active agent.

2. A method for treating hemophilia B in an individual in need thereof consisting essentially of administering to the individual an effective amount of a composition comprising recombinant factor XIII in conjunction with administering to the individual an effective amount of a factor IX.

* * * * *